US00PP10473P

United States Patent [19]

Lemon

[11] Patent Number: Plant 10,473

[45] Date of Patent: Jun. 30, 1998

[54] VARIETY OF GERANIUM PLANT NAMED 'BUBBLE GUM'

[75] Inventor: David Lemon, Lompoc, Calif.

[73] Assignee: John Bodger & Sons Company, So. El Monte, Calif.

[21] Appl. No.: 724,705

[22] Filed: Oct. 1, 1996

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Fulwider Patton Lee Utecht, LLP

[57] ABSTRACT

The cultivar is characterized by its very dark green foliage and clean, rich pink bloom with prominent magenta eye. Its relatively strong growth habit, quick rooting time and continuous flowering provide for superb cuttings and also for quick recovery following wet weather conditions. Bubble Gum is very heat tolerant, and its blooms are slow to shatter and exhibit good post-harvest quality.

1 Drawing Sheet

BACKGROUND OF THE NEW PLANT

The present invention comprises a new and distinct cultivar of *Pelargonium×hortorum* known by the varietal name Bubble Gum (Oglevee No. 2144, Bodger No. 2GM 118-2). The new variety was discovered in a selective breeding program by David Lemon at Bodger Seeds, Ltd., Lompoc, Calif. The new variety is a selection from the crossing of Rio (Bodger No. 10 GM 69 unpatented) which has a rose-pink and red bicolored flower, with Bodger No. 1 GM 33 (unpatented) which has a lavender pink, semi-doubled flower as compared to the claimed cultivar which has a dark pink and magenta bicolored, single flower.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelargonium×hortorum.*

*Commercial.*—Florist's zonal geranium Bubble Gum (Florist's geraniums are a high quality plant which also grows well outdoors).

Form: Uniform, medium mound habit.

*Height.*—19.0–22.0 cm from top of the pot.

*Growth.*—Free basal branching, sturdy stems, leaf petioles and flower peduncles.

*Strength.*—Single floret form is less prone to shattering, free and early flowering, does not need artificial support, very heat tolerant.

Foliage: Stalked leaf attachment; very dark green foliage; no distinct zone present.

Leaves:

*Size.*—Fully expanded leaf 8.5–10 cm.

*Shape.*—Reniform; cordate base.

*Margin.*—Crenate.

*Texture.*—Pubescent; slightly reflective; leathery.

*Color.*—Top: Yellow-Green Group 147A. Bottom: Green Group 137C. Zone: Not present (however plants under stress may exhibit a slightly darker zone area).

*Ribs and veins.*—Venation: Palmate. Color: Yellow-Green Group 146B.

Petioles:

*Length.*—6.0—8.0 cm.

*Color.*—Yellow-Green Group 146B.

Stem:

*Color.*—Yellow-Green Group 146B. Internode length: 2.5–4.0 cm.

The Bud (Umbel)

Shape: Upright; hemispherical cluster.

Size: 3.0–4.0 cm across; tight bud—no color showing.

Inflorecence

Blooming habit: Single; continuous blooming.

Borne: Umbel; florets on pedicel, pedicel on peduncle; 4.0–8.0 cm above foliage.

Closed florets:

*Bud size.*—1.0–1.5 cm in length; 0.6–0.8 cm in width; bud just showing color.

Size:

*Fully open bloom.*—8.5–10 cm across; about 26 florets appearing per inflorescence.

Open florets:

*Form.*—Flat to slightly reversed cupping; open form giving floret a "windmill" look.

*Color.*—Top: Red Group 55B.
*Bottom.*—Red Group 55C.
*Eye.*—Red-Purple Group 57A; Eye on upper two petals has some feathering and is much larger than the smaller eye on lower three petals.
*Petals.*—Five in number.
*Size.*—4.0–4.5 cm across.
*Texture and appearance.*—Velvety; appearance from a distance is a clean, rich pink flower with a prominent magenta eye above very dark green foliage.

Petaloids:
*Quantity.*—None present.

Pedicel:
*Length.*—3.0–3.5 cm.
*Color.*—Greyed-Purple Group 183B.

Peduncle:
*Length.*—14.5–16.0 cm; arises from the node opposite the leaf petiole.
*Color.*—Yellow-Green Group 146B.

Persistence:
*Disease resistance.*—Not Known.
*Lasting quality.*—Less shattering than current market variety "Rio".

Reproductive Organs

Stamens:
*Anthers.*—Length: 2.0–3.0 mm.
*Filaments.*—Length: 7–9 mm. Color: White with very pale pink tips.
*Pollen.*—Golden Brown.

Pistils:
*Number.*—One.
*Length.*—0.8–1.0 cm.
*Stigma.*—Color: Red-Purple Group 60B; 5–6 parted.
*Style.*—Length: 3–4 mm. Color: Red-Purple Group 60B.
*Ovaries.*—Color: Yellow-Green Group 146C; pubescent. Length: 5–6 mm.

Fruit: None.

General Characteristics

Bubble Gum is a new and distinct color addition to the Oglevee Candy series. The bright magenta eye sets off the clean pink color and the dark green foliage adds to the overall attractiveness. When compared to the current market variety Rio, Bubble Gum is a more vigorous plant, produces more cuttings, endures outdoor conditions better and is slower to shatter.

I claim:

1. A new and distinct variety of geranium plant, substantially as shown and described.

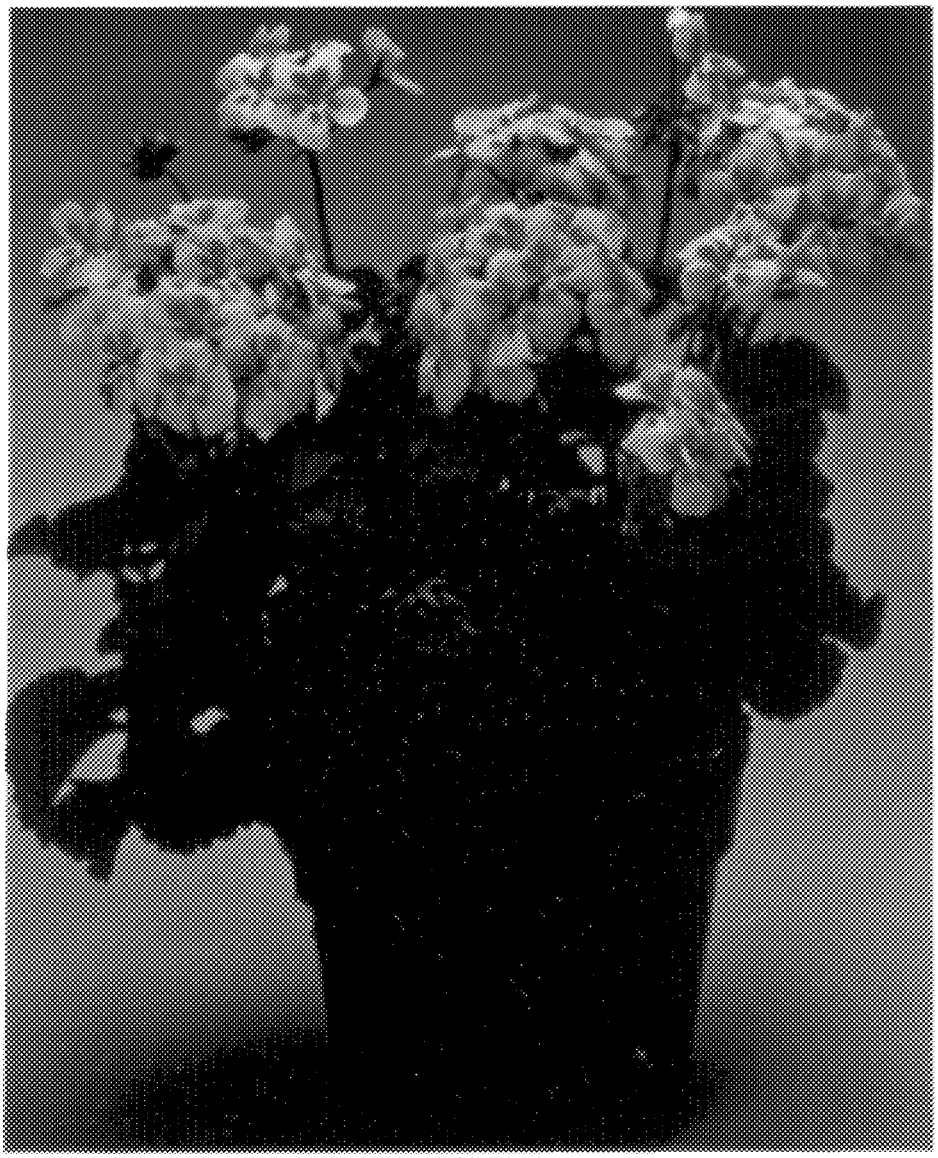

* * * * *